United States Patent [19]
Farnio

[11] Patent Number: 5,152,741
[45] Date of Patent: Oct. 6, 1992

[54] SURGICAL CHEST DRESSING

[75] Inventor: Frank G. Farnio, Shaker Heights, Ohio

[73] Assignee: Golda, Inc., Beachwood, Ohio

[21] Appl. No.: 749,549

[22] Filed: Aug. 23, 1991

[51] Int. Cl.⁵ ............................................. A61F 13/00
[52] U.S. Cl. ...................................... 602/79; 602/61; 602/19; 450/1; 450/63
[58] Field of Search ............... 450/1, 58, 63, 65, 76, 450/88; 602/19, 58, 61, 79

[56] References Cited

U.S. PATENT DOCUMENTS

| | | | |
|---|---|---|---|
| 2,443,127 | 6/1948 | Abeles | 2/42 |
| 2,662,522 | 4/1949 | Muller | 128/155 |
| 2,800,902 | 6/1957 | Wiltrout | 128/167 |
| 2,890,702 | 6/1959 | Farino | 128/460 |
| 3,001,526 | 9/1961 | Krieger | 450/65 |
| 3,399,669 | 9/1968 | Kaplan | 128/78 |
| 3,561,442 | 2/1971 | Goswitz | 128/157 |
| 3,957,057 | 5/1976 | Farino | 128/478 |
| 3,968,803 | 2/1976 | Hyman | 128/482 |
| 4,314,569 | 2/1982 | Speno | 450/1 |
| 5,098,331 | 3/1992 | Corrado | 450/58 |

FOREIGN PATENT DOCUMENTS 597485   1/1948   United Kingdom .
0674354  6/1952   United Kingdom .................. 450/63

Primary Examiner—Paul Prebilic
Attorney, Agent, or Firm—Body, Vickers & Daniels

[57] ABSTRACT

A surgical dressing is constructed of a chest encircling flexible band formed primarily of a stretchable material with free overlapping ends that engage each other between the breasts of a person about which the dressing has been wrapped. The band includes differential support structure to provide more support for the sides of the user as compared with the remainder of the person about which the band has been wrapped.

25 Claims, 4 Drawing Sheets

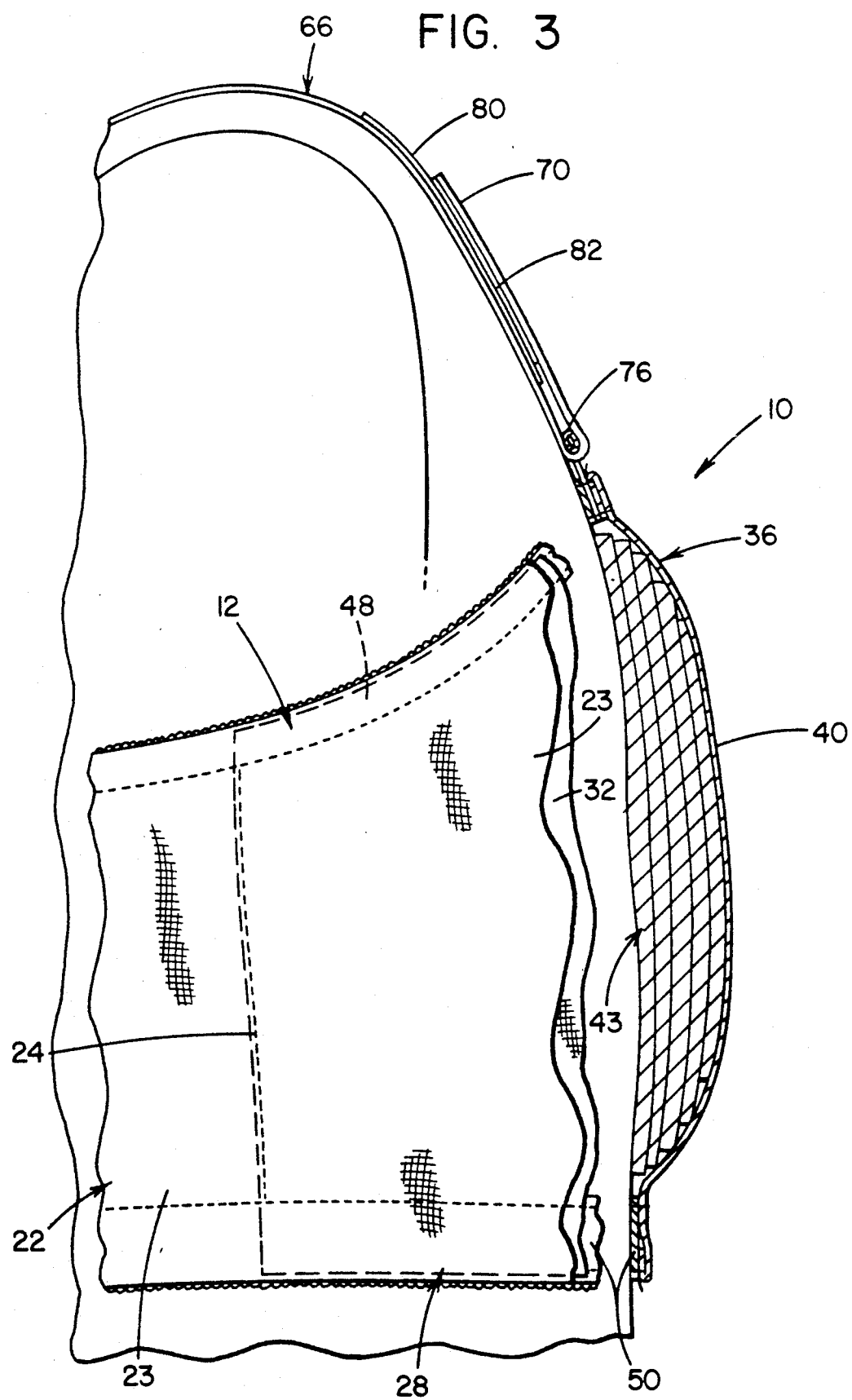

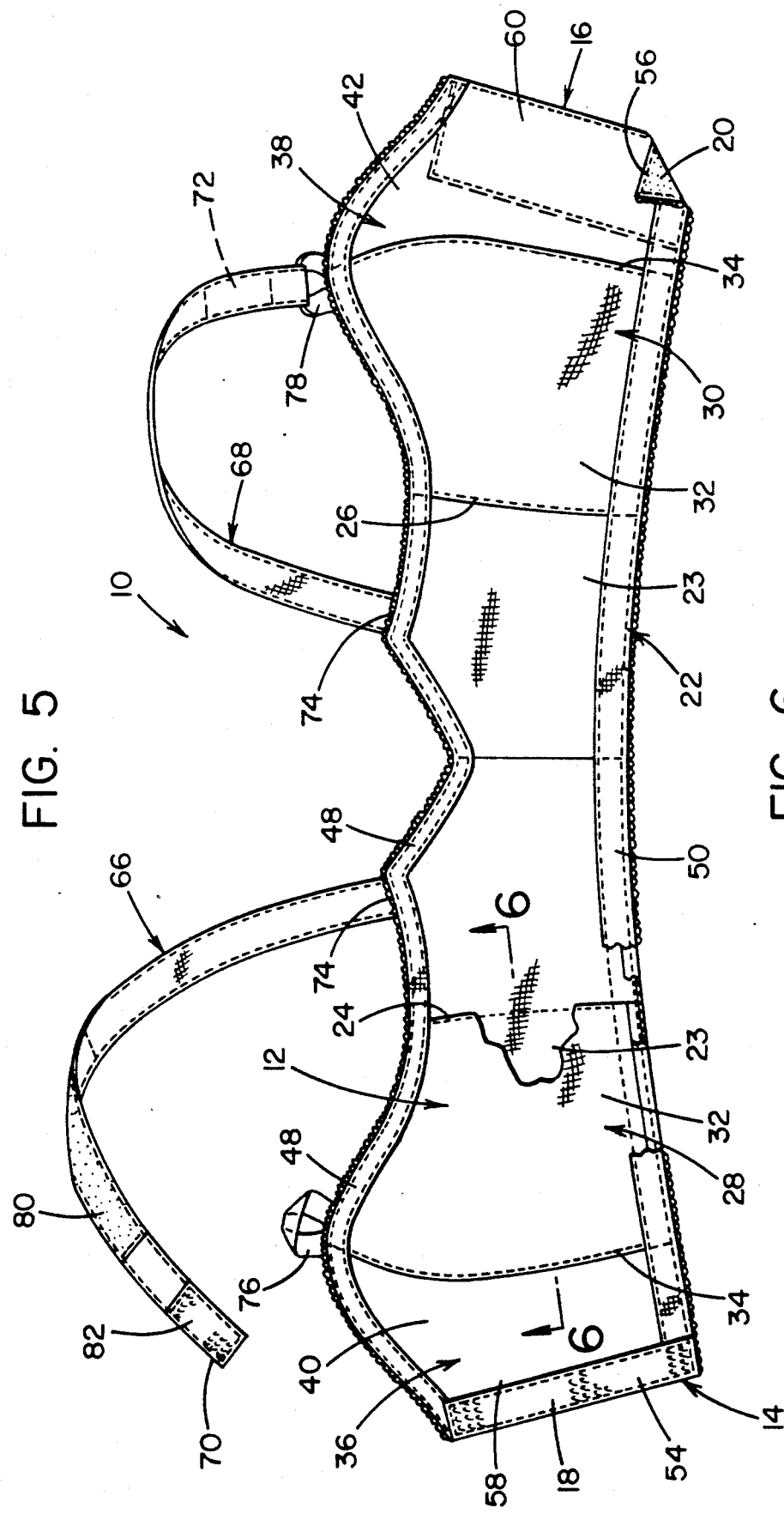

SURGICAL CHEST DRESSING

This invention relates generally to surgical dressings and more particularly to surgical chest dressings. The invention is particularly applicable for a surgical chest dressing used on a post operative patient subsequent to chest surgery and will be described with particular reference thereto. However, the invention may have broader applications and could be used in theory for generally supporting the breasts of a wearer.

BACKGROUND OF THE INVENTION

After a chest operation such as a mastectomy operation, the patient is normally bandaged with an absorbent material over the incision and wrapped with an elastic band or dressing of the type disclosed in U.S. Pat. No. 3,968,803 to Hyman entitled "Surgical Chest Dressing". The Hyman patent is owned by a common assignee with this application and the disclosure thereof is incorporated herein by reference.

Elastic bands are deficient in many cases because they distort the unoperated breast and sometimes restrict the normal respiration of the patient involving expansion and contraction of the chest. Moreover, the patient has to be held in a partially upright position to apply the elastic band which is often quite uncomfortable. Also, when the dressing has to be changed, it is a complex procedure which can not be done by the patient or an untrained person.

To overcome these limitations, a dressing as disclosed in the patent to Hyman was adopted as a substitute for the elastic band. While providing substantial improvements over the elastic band, there still remains several problems which can adversely effect the comfort and overall usefulness of the chest dressing described in the Hyman patent. In this respect, after a mastectomy operation the muscles along the sides of the patient, which have been injured and/or traumatized by the operation, need support to reduce movement and, therefore, the significant discomfort which postoperative patients often experience. At the same time, the support cannot be such that the user has difficulty in breathing or that body movement is overly restricted. Also, in some circumstances, the chest dressing disclosed in the patent to Hyman presses against the absorbent bandages applied to the incision on one or both breasts and presses the breasts against the patient's chest so that the outer sides of the breasts bulge outward and cause both physical and psychological discomfort. In some circumstances too, the pressure of the dressing against the breasts causes the flesh surrounding the breasts to withdraw under the arms of the patient. Again, this is quite uncomfortable for the user. This can also happen when the patient has excess flesh under her arms and along her sides which naturally tends to bulge out when the breasts are pressed against her chest by the dressing.

Another deficiency in the device disclosed in the patent to Hyman relates to the shoulder straps which are connected at one end to the rear of the band wrapped around the patient and are adjustably fastened to the front of the band so as to lie over the shoulders of the patient and support the band against slipping downwards. However, in practice the straps tend to cause the wrapped band to move upwards and downwards, thus causing discomfort for the wearer. Further, the elastic material is generally rough and uncomfortable and tends to cut into and irritate the shoulders of the user.

Still another deficiency relating to the shoulder straps is that the fasteners for the straps, i.e. VELCRO fasteners, were positioned near the rear of the band which prevented the patient from easily and independently adjusting the length of the straps.

SUMMARY OF THE INVENTION

The present invention is generally directed to an improved surgical chest dressing which provides differential support and incorporates wearer comfort.

In accordance with the invention a surgical chest dressing is formed of a chest encircling flexible band of stretchable material with free ends which engage each other between the breasts of a user about which the dressing is wrapped. The band is constructed so as to provide more support along the sides of the user's body as compared with the support generally provided for the breasts and the back of the user's body. In addition, the band provides additional side support to the non-operated breast in the lateral pectoral region.

In accordance with the invention, the band has a back portion of single ply stretchable material which is disposed against the back of a user. The back portion has two longitudinally spaced ends which are each connected to the rear end of one of a pair of side panels. The side panels are of double ply, stretchable, non-elastic material which lies against the sides of the user including the sides of the user's breasts. The side panels each have front ends which are spaced from the back portion and are connected to a corresponding one of a pair of front flaps. The front flaps are of single ply, stretchable, non-elastic material and support the breasts of the user. The front flaps have free ends which overlap each other and are releasably secured together.

Further in accordance with the invention, a pair of shoulder straps are secured to the back portion of the band. Loops secured to the upper portion of the front and side panels receive the loose ends of the straps. Fasteners are provided on the straps for releasably securing the straps when they are passed through the loops and disposed against the shoulders of the user. Preferably, the shoulder straps can be secured near the loops on the chest of the user and at variable positions so that the user can easily adjust the fit to achieve the maximum comfort.

Still further in accordance with the invention, the comfort of the shoulder straps is enhanced by constructing the straps of substantially non-elastic and non-stretchable material, whereby the dressing remains substantially stationary on the user without the vertical movement occasioned by the elastic straps of the prior art devices. Moreover, the shoulder straps are constructed with a soft lining affixed to the non-elastic, non-stretchable material. The soft lining is disposed so as to place the weight of the supported breasts on the shoulders of the user without causing irritation of the skin as with the prior elastic shoulder straps. To still further increase the user's comfort, a soft foam material is provided between the lining and the non-elastic, non-stretchable material for reducing the tendency of the straps to cut into the user's shoulders.

It is thus a principal object of the present invention to provide a surgical chest dressing which provides differential support of the back, sides and breasts of the user.

It is another object of the present invention to provide a surgical chest dressing wherein more lateral side support is provided for the sides of a patient and for the sides of the unoperated breast by the side portions of the dressing as compared with the back or front of the dressing.

It is still another object of the present invention to provide a surgical chest dressing incorporating shoulder straps of non-elastic, non-stretchable material which are soft and reduce the tendency to cut into and irritate the shoulders of the wearer.

It is yet a further object of the present invention to provide a surgical chest dressing in which the shoulder straps are secured above the breasts of the user in selectable, user adjustable positions.

These and other objects and advantages of the present invention will become apparent from the following description taken in conjunction with the accompanying drawings which are described below.

BRIEF DESCRIPTION OF THE DRAWINGS

The invention may take physical form in certain parts and arrangements of parts, preferred embodiments of which will be described in detail and illustrated in the accompanying drawings which form a part hereof and wherein:

FIG. 3 is a view through line 3—3 of FIG. 1 illustrating the single ply construction of the front flaps of the dressing being worn by a patient;

FIG. 5 is a plan view of the outer side of the preferred embodiment of the present invention in an opened condition; and FIG. 6 is a view through line 6—6 of FIG. 5 illustrating the relationship between the back portion, a side panel and a flap of the chest dressing.

DETAILED DESCRIPTION OF THE INVENTION

Figure 1:
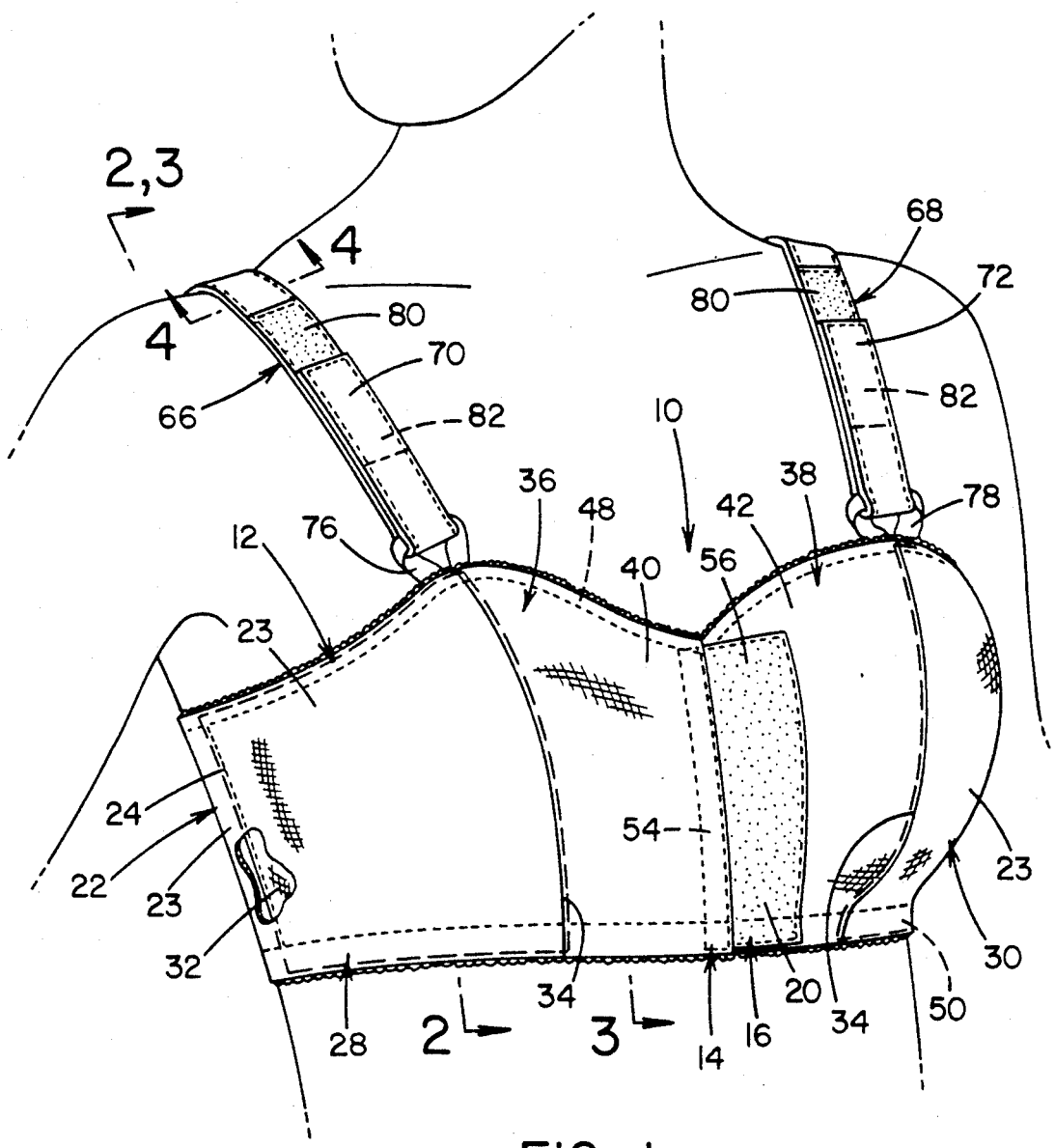
FIG. 1 is a perspective view showing a patient wearing the preferred embodiment of the surgical chest dressing in the secured position.

Referring now to the drawings wherein the showings are for the purpose of illustrating the preferred embodiment of the invention only and not for the purpose of limiting same, FIGS. 1 and 5 illustrate a surgical chest dressing 10 having a chest encircling flexible band 12 primarily formed from a stretchable material and principally used for mastectomy patients. Band 12 has free ends 14 and 16 which overlap each other at engaging surfaces 18 and 20 between the breasts of the person about which the dressing 10 has been wrapped. In general, the dressing of the present application will deform upon application and exert very little force on the users. To better perform this function, adjustable fastening means, such as VELCRO are provided on the engaging surfaces because they can be adjusted to a large number of positions so that the chest dressing can properly engage and retain an inner bandage while not distorting or exerting undue pressure on the unoperated breast. A significant aspect of the invention is that the flexible band 12 includes differential support providing structural components which provide more support for the sides of the user's body and for the sides of the unoperated and the operated on breast as compared with the support generally provided for the breasts and back of the user's body.

In accordance with the preferred embodiment of the invention, the chest dressing which may be referred to as a bandage, includes a flexible band 12 formed primarily from a stretchable, but non-elastic fabric or material. Stretchable material conforms to the shape which it overlays without exerting substantial pressure. An elastic material, on the other hand, will conform to the surface it overlays but will exert a pronounced pressure on the surface because of its tendency to return to its original shape. The return force of a stretchable material as defined here is very small when compared to that of an elastic material. This definition is well known in the art and in practice one such stretchable material is a loose weave, porous 100% knit nylon which allows freedom of movement of the material in all directions and a low recovery force so that the material does not exert substantial pressure on the patient wearing the dressing or bandage.

Flexible band 12 includes a back engaging portion 22 which is longitudinal and continuous without fasteners or other coupling devices. Although band 12 is preferably stretchable material throughout its length, it is possible to provide certain areas with other material without departing from the intent of the invention. The back portion 22 is constructed of a single ply of stretchable, but non-elastic material 23 for supporting the wearer's back when the dressing is wrapped around the wearer's body. The back portion has two longitudinally spaced ends defined by stitching 24 and 26 by which side panels 28 and 30 are respectively connected to material 23.

Figure 2:
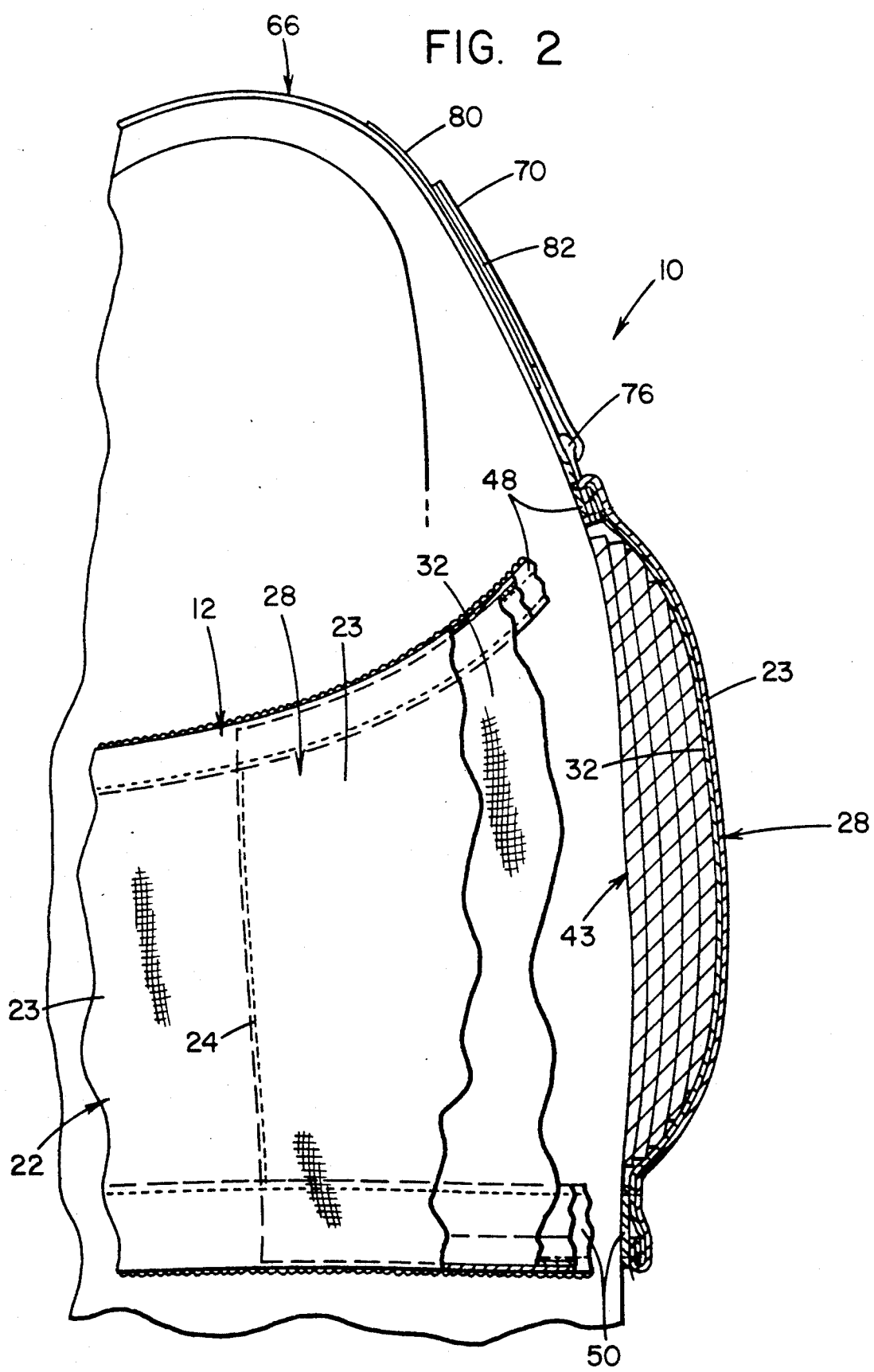
FIG. 2 is a view through line 2—2 of FIG. 1 illustrating the double ply construction of the side panel of the dressing being worn by a patient.

As shown in FIGS. 2 and 6 with respect to side portion 28, each of the side panels is a two ply layer of stretchable, non-elastic material. Preferably, one of the layers is provided by an extension of material 23 beyond stitching 24 and 26, and the second layer is provided by a panel of material 32 overlying the corresponding extension of material 23. Each of the panels 32 is connected to the corresponding extension of material 23 by stitching 24 or 26 at one end and stitching 32 of the other end. Front flaps 36 and 38 are connected to side panels 28 and 30, respectively, by stitchings 34, and the front flaps are defined by panels 40 and 42 of single ply, stretchable, non-elastic material.

Referring to FIG. 1, it can be seen that the side panels 28 and 30 lie against the sides of a user. Specifically, the sides include the sides of the chest as well as the sides of the user's breasts. The double ply construction provides added support for the muscles in the side of the user which are often damaged and/or sore from the operation. The additional support enables the user to move about while the restricting the movement of her sides and side muscles. At the same time, the support is not such that the patient's breathing is restricted or the patient has an unnatural feeling of being bound about the chest which could be psychologically demoralizing in the post operative period following a mastectomy operation. Another advantage of the extra support provided by the side panels is improved comfort when the absorbent bandages applied directly to the user's chest cause flesh to protrude outward from the sides. The latter can produce an uncomfortable feeling which is partially relieved with the additional support against movement of the side while the wearer is walking or otherwise moving about. The flesh tissue surrounding the unoperated on and/or operated on breast is also supported to reduce the tendency of the tissue from withdrawing under the arms of the wearer. Another advantage to the double ply construction is the additional support given to the underlying bandages, designated generally by the numeral 32 in FIGS. 2 and 3. That is, the bandages covering the breast which was operated on are firmly held in place along the patient's sides, spaced away from the actual location of the incision and thereby do not exert too much pressure near the tender location of the incision.

An undulating upper marginal strip 48 is provided around the upper portion of flexible band 12. In a like manner, a generally straight lower marginal band 50 is provided along the lower portion of flexible band 12. These two marginal strips are formed from elastic material which provides strength for the bandage or dressing in the longitudinal direction so that the bandage holds as generally shown in FIG. 5.

The ends of front flaps 40 and 42 spaced from stitchings 34 provide the free ends 14 and 16 of band 12 that overlap when the dressing or bandage is in place around a patient. The engaging surfaces 18 and 20 of these free ends are provided with a two element, contact sensitive, reusable fastening structure to provide selectable longitudinal positions within a given general range determined by the elements forming the fastening structure. The fastener include no metal elements and is, in the preferred embodiment, as illustrated in FIG. 5, a VELCRO fastener wherein the first element 54 providing surface 18 is a transversely extending gripping strip including a number of small, outwardly extending, closely spaced flexible hooks which take on the appearance of a rough fabric. The second element 56 providing surface 20 is a fabric strip extending transversely of flexible band 12 and, as is well known, interlocks with the hooks of gripping strip 54. This second element assumes the normal appearance of a velvet fabric. Strips 54 and 56 are non-elastic and non-stretchable to provide transverse stability for the bandage or dressing. These strips extend between the elastic strips 48 and 50 to complete the boundary for band 12 and provide the final dimensional stability and general strength for the band. The overlapping surfaces onto which elements 50 and 52 are provided are designated 58 and 60 respectively, in FIG. 5. These overlapping surfaces are at the free ends 14 and 16 of front flaps 36 and 38.

Referring now more particularly to the front flaps 36 and 38, as seen in FIGS. 1 and 5, they are constructed of a single ply of stretchable material. This material supports the bandaged, closed incision on an operated on breast as well as the non-operated on breast of a mastectomy patient. A single ply of stretchable material is preferred for the front flap since it is desirable that the material be able to stretch out and accommodate different sized breasts as well as bandages which cover the incision from the operation. Accordingly, the extra support which is achieved with the present design is from the two ply construction on the side panels as discussed before.

Front flaps 36 and 38 are joined to side panels 28 and 30, respectively by seams 34 as described herein before, and these seams are longer than the non-stretched, transverse dimension between strips 48 and 50 so that forwardly extending profiles are created at the forward portions of front flaps 36 and 38. This forward contour allows better conformity to the underdressing on a closed incision and to the non-operated breast of a mastectomy patient.

As so far described, flexible band 12 can be wrapped around a post surgical patient and connected at the front by strips 54 and 56. The strips are secured together by engaging strip 54 at a selected position on strip 56. To further support the dressing or bandage on the postoperative patient, two spaced shoulder straps 66 and 68 are provided. These straps include loose ends 70 and 72, respectively, and are secured by seams 74 to back portion 22 of band 12. This is a fixed fastening arrangement so that no manipulation is needed under the patient when the bandage or dressing 12 is applied around a surgical patient as shown in FIG. 1. Straps 66 and 68 are adjustably secured to the front flaps and side panels by an appropriate fastening arrangement which involves no metal clips and can be easily manipulated to adjust the proper position of the bandage, even by the patient. In accordance with the preferred embodiment, loops 76 and 78 are affixed so as to straddle the seam between the front flaps and the side panels, and ends 70 and 72 of the straps are provided with VELCRO fastening strips 80 an 82. The loops are formed from non-elastic, non-stretchable cloth and are secured onto elastic marginal strip 48 adjacent the larger transverse dimension of the band 12. To fasten the straps in an effective adjusted length, the loose ends 70 and 72 are passed through loops 76 and 78 and the fastening strips 80 and 82 brought into engagement with one another. In the illustrated embodiment, strips 80 are formed from the engaging fabric of the VELCRO fastener and strips 82 include the small gripping hooks. A significant aspect of the invention lies in the positioning of the fastening strips 80 and 82. As illustrated in FIG. 1, once the band 12 is in place around the patient, the shoulder straps can be adjusted with the fastening strips which are provided in the front of the patient, above the breasts, where they can be easily seen and readjusted solely by the patient.

Figure 4:
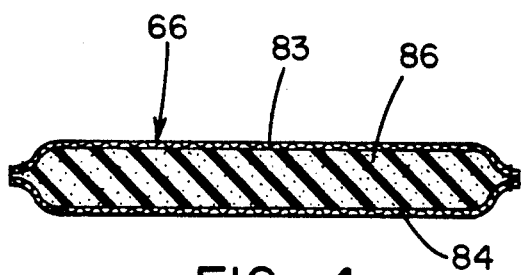
FIG. 4 is a view through line 4—4 of FIG. 1 illustrating the construction of the shoulder straps.

Another important aspect of the invention resides in the preferred construction of the shoulder straps 66 and 68 from substantially non-elastic, non-stretchable material whereby the dressing 10 remains substantially stationary on the person using the dressing. This feature of providing shoulder straps which merely support the flexible band 12 without any biasing that resides in the stretchable shoulder straps of the prior art, provides support without causing the discomfort associated with the band moving about, typically up and down, on the patient. Further, the shoulder strips are constructed of two layers of material 82 and 84 as seen in FIG. 4. The inner layer 84 is a soft material which contacts the body of the patient and reduces discomfort or irritation caused by the movement of the straps against the body of the person using the dressing. Typically, the inner layer is of a soft cotton material. The cotton material also prevents the shoulder straps from slipping. To further reduce discomfort of a person using the dressing, a soft foam rubber or rubber like material 86 is disposed between the layers of material 82 and 84 for preventing the shoulder straps from pressing into the shoulders of the wearer.

Referring now to FIG. 1, a surgical patient is illustrated with arms extended. An absorbent dressing, such as dressing 43 shown in FIG. 2, is placed over the closed incision and taped lightly to hold the absorbent dressing in place. Thereafter, the flexible band 12 is placed under the patient with the back portion engaging the back of the patient and side panels 28 and 30 extending loosely to either side generally under the arms. Thereafter, the front flaps 36 and 38 are brought together and snugly secured by elements 54 and 56 in front of the patient as shown in FIG. 1. Loose ends 70 and 72 of straps 66 and 68 are brought over the shoulders of the patient and passed from the back through loops 76 and 78, after which strips 80 and 82 are engaged to fasten the straps. To change the dressing, it is only necessary to loosen the shoulder straps and open the front of the dressing. This can be done quite easily by a relatively untrained person. By providing the extra support along the sides of the patient, movement of the injured muscles and/or the flesh or sides of one or both breasts itself is restricted and the wearer feels much more comfortable. Also, the shoulder straps support band 12 without cutting into and otherwise hurting the patient's shoulders. At the same time, the combination of the double ply material in the side panels with the single ply material in the back portion and front flaps enables the respiration of the patient to be unaffected and prevents undue pressure on the bandage covering the incision.

The invention has been described with reference to a preferred embodiment and it is apparent that many modifications can be incorporated into the design and assembly of the surgical chest dressing disclosed herein without departing from the sphere or essence of the invention. It is intended to include all such modifications and alterations insofar as they come within the scope of the present invention.

Having thus described the invention, it is claimed:

1. A surgical chest dressing comprising:
   a chest encircling flexible band formed primarily from a stretchable material, said band having free ends overlapping each other at engaging surfaces between the breasts of a person about which the dressing has been wrapped; and
   said band including differential support means for providing more support for the sides and sides of said breasts of said person as compared with the support provided for the front of said breasts and back of said person.

2. A surgical chest dressing as defined in claim 1 wherein said band has a back portion of a single layer of stretchable material adapted to lie against the back of said person;
   said back portion having two longitudinally spaced ends, with each of said ends being connected to a different one of a pair of side panels, said side panels being formed of a double layer of stretchable, non-elastic material and adapted to lie against the sides and sides of the breasts of said person, said side panels each having front ends spaced from said back portion and connected to a corresponding one of a pair of front flaps;
   said front flaps including said free ends and being formed of a single layer of stretchable, non-elastic material adapted to support the breasts of said person; and
   fastening means for releasably securing said free ends together.

3. A surgical chest dressing as defined in claim 2 including first and second shoulder straps, each of said straps being fixedly secured onto said back portion; and
   means on each of said side panels and corresponding front flap for securing a corresponding one of said straps thereto.

4. A surgical chest dressing as defined in claim 3 wherein each said strap has a loose end and each said side panel and corresponding front flap has an upper portion;
   said strap securing means including a loop element secured to each said upper portion to receive the loose end of the corresponding strap; and
   a first fastener element on each said strap at a position spaced from said loose end and a second fastening element on each said strap adjacent said loose end and releasably interengagable with said first fastening element.

5. A surgical dressing as defined in claim 3 wherein each said first and second shoulder strap includes a layer of substantially non-elastic and non-stretchable material.

6. A surgical dressing as defined in claim 5 wherein each said first and second shoulder straps includes a layer of soft lining material attached to said non-elastic, non-stretchable material for engaging the body of the person using the dressing.

7. A surgical dressing as defined in claim 6, wherein each said first and second should straps includes a soft foam material disposed between said lining and said non-elastic, non-stretchable material.

8. A surgical dressing as defined in claim 3 wherein each said first and second straps includes interengaging fastening means for varying the effective length of said strap.

9. A surgical dressing as defined in claim 3 wherein said means for releasably securing said free ends together includes a two element, contact sensitive, adjustable fastening means with each of said two elements being secured to a different one of said engaging surfaces of said overlapping free ends.

10. A surgical chest dressing, comprising:
    a chest encircling flexible band formed primarily from a stretchable material, said band having a back portion adapted to lie against the back of a person using said dressing;
    said back portion having longitudinally spaced ends, with each of said ends connected to a corresponding one of a pair of side panels adapted to engage and exert supporting pressure against the sides and sides of the breasts of the person using the dressing;
    said side panels including front ends spaced over the width of said band and from said back portion and connected to a corresponding one of a pair of front flaps adapted to support the breasts of the person using the dressing, said flaps including free ends overlapping each other at engaging surfaces when said dressing is wrapped around said person;
    fastening means for releasably securing said free ends together;
    first and second shoulder straps fixedly secured to said back portion; and
    means on each of said front flaps and the corresponding side panel for releasably securing said straps thereto.

11. A chest dressing as defined in claim 10 wherein said front flaps and said back portion are each formed of a single layer of a stretchable, non-elastic material and each of said side panels is formed from two layers of stretchable, non-elastic material, whereby said side panels provide more support for the sides and sides of the breasts of the person using the dressing as compared with the support provided by the back portion and front flaps of the dressing, said side panels and said front flaps connected on said side of said breast.

12. A chest dressing defined in claim 10 wherein each said shoulder strap has a loose end and each said front flap and corresponding side panel has a corresponding upper portion, the strap securing means on each of said front flaps and corresponding side panels including a loop element secured to said upper portion and adapted to receive said loose end; and a first fastening element on said strap at a position spaced from said loose end, and a second fastening element on said strap adjacent said loose end and releasably engagable with said first element to secure said loose end to said loop element.

13. A chest dressing as defined in claim 12 wherein, said first and second fastening elements are interengagable to adjust the effective length of said shoulder strap.

14. A chest dressing as defined in claim 10 wherein said fastening means for releasably securing said free ends includes a two element, contact sensitive, adjustable fastening means with each of said two elements being secured to a different one of said engaging surfaces of said overlapping free ends.

15. A chest dressing as defined in claim 10 wherein each of said front flaps has a non-stretched transverse dimension at a position adjacent said fastening means, and said side panels are connected to said front flaps with a seam which is substantially longer than said transverse dimension, whereby said front flaps assume a non-stretched outwardly protruding profile.

16. A chest dressing as defined in claim 10 wherein said stretchable material is stretchable in all directions.

17. A chest dressing as defined in claim 10 wherein said back portion, said side panels and said front flaps include upper and lower longitudinally extending edges and elastic body engaging bands secured to said edges.

18. A surgical dressing as defined in claim 10 wherein said first and second shoulder straps include a layer of substantially non-elastic and non-stretchable material.

19. A chest dressing as defined in claim 18 wherein said first and second shoulder straps include a layer of soft lining material attached to said non-elastic, non-stretchable material for engaging the movement of the body of the person using the dressing.

20. A chest dressing as defined in claim 19 wherein a soft foam rubber material is disposed between said soft lining material and said non-elastic, non-stretchable material.

21. A surgical chest dressing as defined in claim 4 wherein said strap first and second fastening elements are interengagable between the breast and shoulder of said person.

22. A surgical dressing as defined in claim 21 wherein said means for releasably securing said free ends together includes a two element, contact sensitive, adjustable fastening means with each of said two elements being secured to a different one of said engaging surfaces of said overlapping free ends.

23. A surgical chest dressing as defined in claim 2 wherein said side panel consists of a first and second layer of non-elastic stretchable material, said second layer spaced over the complete width of said band and extending between said back portion and said front flap, said side panel and said front flap connected on said side of said breast.

24. A surgical chest dressing as defined in claim 12 wherein said strap first and second fastening elements are interengagable between the breast and shoulder of said person.

25. A chest dressing as defined in claim 23 wherein said fastening means for releasably securing said free ends includes a two element, contact sensitive, adjustable fastening means with each of said two elements being secured to a different one of said engaging surfaces of said overlapping free ends.

* * * * *